(12) United States Patent
Kirschman (10) Patent No.: US 8,241,342 B2
(45) Date of Patent: Aug. 14, 2012

(54) FLEXIBLE CRANIAL CLAMP AND METHOD OF ANCHORING TO CRANIUM

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 943 days.

(21) Appl. No.: 12/117,973

(22) Filed: May 9, 2008

(65) Prior Publication Data
US 2008/0281339 A1 Nov. 13, 2008

Related U.S. Application Data

(60) Provisional application No. 60/917,423, filed on May 11, 2007.

(51) Int. Cl.
*A61B 17/04* (2006.01)
(52) U.S. Cl. .......................................... 606/324
(58) Field of Classification Search .............. 606/75, 606/219, 324; 411/326–331
See application file for complete search history.

(56) References Cited

U.S. PATENT DOCUMENTS

| | | | |
|---|---|---|---|
| 4,075,924 A * | 2/1978 | McSherry et al. | 411/112 |
| 5,578,036 A | 11/1996 | Stone et al. | |
| 5,916,200 A | 6/1999 | Eppley et al. | |
| 6,068,631 A | 5/2000 | Lerch | |
| 6,379,363 B1 | 4/2002 | Herrington et al. | |
| 6,685,707 B2 | 2/2004 | Roman et al. | |
| 2002/0156475 A1* | 10/2002 | Lerch et al. | 606/70 |
| 2004/0102779 A1* | 5/2004 | Nesper et al. | 606/72 |

* cited by examiner

*Primary Examiner* — Thomas Barrett
*Assistant Examiner* — Melissa A Golob
(74) *Attorney, Agent, or Firm* — Jacox, Meckstroth & Jenkins (57) ABSTRACT

A flexible clamp for plugging an aperture in a bone, including a plurality of flexible anchoring members, where each flexible anchoring member has a first end and a second end opposite the first end; a locking tab connected to the second end of each flexible anchoring member; and, a stabilization member slidingly engagable with the flexible anchoring members, wherein the stabilization member may be translocated from a position adjacent the first ends of the flexible anchoring members to a clamping position adjacent the second ends of the flexible anchoring members. The locking tabs engage an inner surface of the bone and the stabilization member engages an outer surface of the bone when in the clamping position. The flexible clamp further includes a ratcheting mechanism associated with each flexible anchoring member, and a plurality of pawl mechanisms formed within the stabilization member which lockingly engage with each of the ratcheting mechanisms.

41 Claims, 4 Drawing Sheets

FLEXIBLE CRANIAL CLAMP AND METHOD OF ANCHORING TO CRANIUM

CROSS-REFERENCE TO RELATED APPLICATION

The present application claims priority to provisional U.S. Application Ser. No. 60/917,423 filed May 11, 2007, to which Applicant claims the benefit of the earlier filing date. This application is incorporated herein by reference and made a part hereof.

BACKGROUND OF THE INVENTION

1. Field of the Invention

The present invention relates generally to a clamp for use in plugging holes drilled in bone and, in particular, to a cranial clamp which is utilized to cover a burr hole drilled into a skull.

2. Description of the Related Art

In traditional neurosurgery, large sections of bone are removed from the skull. Once the procedure has been performed, there is a need to anchor the bone section back into place. Several mechanisms for achieving this function have been used, including small metallic plates affixed with screws or wires. Another mechanism has been a rigid cranial clamp which consists of two connected circular plates residing on the inside and outside surfaces of the skull.

More recently, neurosurgeons have been performing operations with a small drilled opening in the skull known as a burr hole. Such operations are less invasive than larger craniotomy procedures where larger sections of bone are removed. It is a goal of the neurosurgeon to plug the burr hole following such a procedure, typically utilizing a metallic circular plate affixed with multiple small screws as demonstrated in U.S. Pat. No. 5,578,036 to Stone et al. and U.S. Pat. No. 5,916,200 to Eppley et al.

Cranial clamps are considered superior to the metallic plates in that they are faster to place, do not involve additional drilling of screw holes into the skull, and do not require downward forces onto the skull with a screwdriver. Exemplary cranial clamps in the art include U.S. Pat. No. 6,685,707 to Roman et al., U.S. Pat. No. 6,379,363 to Herrington et al., and U.S. Pat. No. 6,068,631 to Lerch. While each of these cranial clamps are able to perform the intended function, they do not have the ability to be placed through a burr hole having a diameter smaller than the clamp itself. Such prior art clamps generally require additional devices to assist in placing the clamp in position, which further complicates the procedure.

Thus, it would be desirable for a clamp to be developed for use in plugging a burr hole formed in bone, and particularly a skull, which has the ability to be inserted through such burr hole. It would also be desirable for such clamp to be designed so that it is held rigidly in place without a threaded connection.

SUMMARY OF THE INVENTION

In accordance with a first exemplary embodiment of the invention, a flexible clamp device for the anchoring of cranial bones is disclosed as including a plurality of flexible anchoring members and a stabilization member. Each of the plurality of flexible anchoring members includes an elongated body having an anchoring end and a second end opposite thereof, as well as a unidirectional ratcheting mechanism associated therewith. The flexible clamp device further includes a locking tab extending from the anchoring end of each elongated body adapted to clamp to an internal surface of a cranial bone, where the locking tab includes a first portion extending outwardly from the anchoring end of the elongated body and a second portion extending from the first locking tab portion toward the second end of the elongated body. A cross member is provided to connect the second ends of the elongated bodies, wherein the elongated body of each flexible anchoring member may be flexed such that the anchoring ends thereof are displaceable inwardly to facilitate placement through an aperture in a cranial bone.

The stabilization member further includes a plurality of pawl mechanisms to receive the unidirectional ratcheting mechanism on each elongated body, as well as a plurality of slits formed therein for receiving each elongated body. Accordingly, the stabilization member can be translocated from a first position adjacent the second ends of the elongated bodies to a second position adjacent the anchoring ends of the elongated bodies. The stabilization member in the second position constitutes a rigid clamp with the anchoring ends of the elongated bodies and causes such anchoring ends to be maintained in a spaced position. The stabilization member further includes a plurality of locking teeth extending from a lower surface thereof so as to engage an upper surface of the cranial bone.

In a second exemplary embodiment of the invention, a flexible clamp for plugging an aperture in a bone is disclosed as including: a plurality of flexible elongated bodies, where each elongated body has a first end and a second end opposite the first end; a locking tab connected to the first end of each elongated body; and, a stabilization member slidingly engagable with the elongated bodies, wherein the stabilization member may be translocated from a position adjacent the second ends of the elongated bodies to a clamping position adjacent the first ends of the elongated bodies. The locking tabs engage an inner surface of the bone and the stabilization member engages an outer surface of the bone when in the clamping position. The flexible clamp further includes a cross member connecting the second ends of the elongated bodies in spaced relation, a unilateral ratcheting mechanism associated with each elongated body, and a plurality of pawl mechanisms formed within the stabilization member which lockingly engage with each of the ratcheting mechanisms.

The stabilization member further comprises a substantially planar member slidingly engagable with the flexible elongated bodies and a plurality of locking teeth extending from a lower surface of the planar member in spaced relation which engage the outer surface of the bone when the stabilization member is in the clamping position. The planar member of the stabilization member further includes a plurality of slits formed partially therein for receiving the elongated bodies. The planar member may be any shape, but preferably is sized to cover the aperture in the bone.

The first ends of the elongated bodies are adjustably spaced or compressible when the stabilization member is positioned adjacent the second ends of the elongated bodies. The first ends of the elongated bodies are maintained in spaced relation when the stabilization member is positioned adjacent thereto. Accordingly, the position of the stabilization member along the elongated bodies controls the amount of movement available at the first ends of the elongated bodies. This permits the locking tabs of the elongated bodies to be movable between a position wider than the aperture to a position more narrow than the aperture.

In accordance with a third embodiment of the present invention, a method of positioning a clamp within an aperture in a cranial bone is disclosed, where the clamp includes a plurality of flexible elongated bodies and a stabilization member slidingly engagable therewith, comprising the following steps: maintaining second ends of the elongated bodies in a predetermined spaced position; flexing first ends of the elongated bodies from a predetermined spaced position wider than the aperture to a compressed position more narrow than the aperture; inserting the first ends of the elongated bodies through the aperture in the cranial bone; expanding the first ends of the elongated bodies from the compressed position to the predetermined spaced position so as to engage an inner surface of the cranial bone; and, translocating the stabilizing member from adjacent the second ends of the elongated bodies to a position adjacent the first ends thereof so as to engage an outer surface of the cranial bone. The method may further include the steps of locking the stabilizing member in the position, associating locking tabs with the first ends of the elongated bodies, engaging the stabilizing member with the elongated bodies, and trimming the elongated bodies after the stabilization member engages the outer surface of the cranial bone. The stabilizing member may be engaged with the elongated bodies either prior to or after inserting the first ends of the elongated bodies through the aperture. The flexing step and translocation of the stabilizing member may be performed manually or with a clamping instrument.

In one aspect, one embodiment of the invention comprises a flexible clamp device for the anchoring of cranial bones, comprising a plurality of flexible anchoring members, and a stabilization member.

In another aspect, another embodiment of the invention comprises a method of placing a flexible cranial clamp, wherein the method comprises the steps of identifying a hole or other defect in a cranial bone, i.e. during neurosurgery, flexing of anchoring members of a flexible cranial clamp such that the anchoring members are displaced inward, placing inwardly-displaced locking members through the hole or other defect in cranial bone, and expanding and stabilizing the locking members by translocation of a sliding stabilization member towards the hole or other defect in cranial bone.

In still another aspect, another embodiment of the invention comprises a flexible clamp for plugging an aperture in a bone, comprising a plurality of flexible elongated bodies, each elongated body having a first end and a second end opposite the first end, a locking tab connected to the second end of each elongated body, and a stabilization member slidingly engagable with the elongated bodies, wherein the stabilization member may be translocated from a position adjacent the second ends of the elongated bodies to a clamping position adjacent the first ends of the elongated bodies, wherein each of the locking tabs engage an inner surface of the bone and the stabilization member engages an outer surface of the bone when in the clamping position.

In yet another aspect, another embodiment of the invention comprises a method of positioning a clamp within an aperture in a cranial bone, the clamp including a plurality of flexible elongated bodies and a stabilizing member slidingly engagable therewith, comprising the following steps maintaining second ends of the elongated bodies in a predetermined spaced position, flexing first ends of the elongated bodies from a predetermined spaced position wider than the aperture to a compressed position more narrow than the aperture, inserting the first ends of the elongated bodies through the aperture in the cranial bone, expanding the first ends of the elongated bodies from the compressed position to the predetermined spaced position so as to engage an inner surface of the cranial bone, and translocating the stabilizing member from adjacent the second ends of the elongated bodies to a position adjacent the first ends thereof so as to engage an outer surface of the cranial bone.

In still another aspect, another embodiment of the invention comprises a flexible clamp device for use with a cranial bone, comprising at least one flexible anchoring member for positioning on the cranial bone, and a stabilization member for slidably mounting on the at least one flexible anchoring member to cover a hole or opening in the cranial bone.

These and other objects and advantages of the invention will be apparent from the following description, the accompanying drawings and the appended claims.

DETAILED DESCRIPTION OF THE PREFERRED EMBODIMENTS

Figure 1:
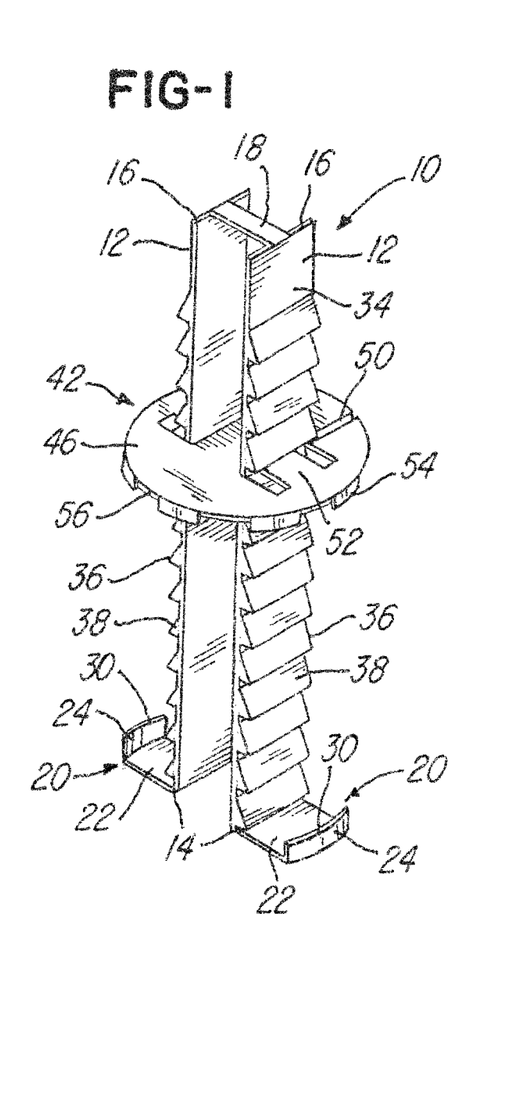
FIG. 1 is a perspective view of a cranial clamp in accordance with the present invention, where the stabilizing member is located in a position midway between the first and second ends of the flexible anchoring members.
Figure 3:
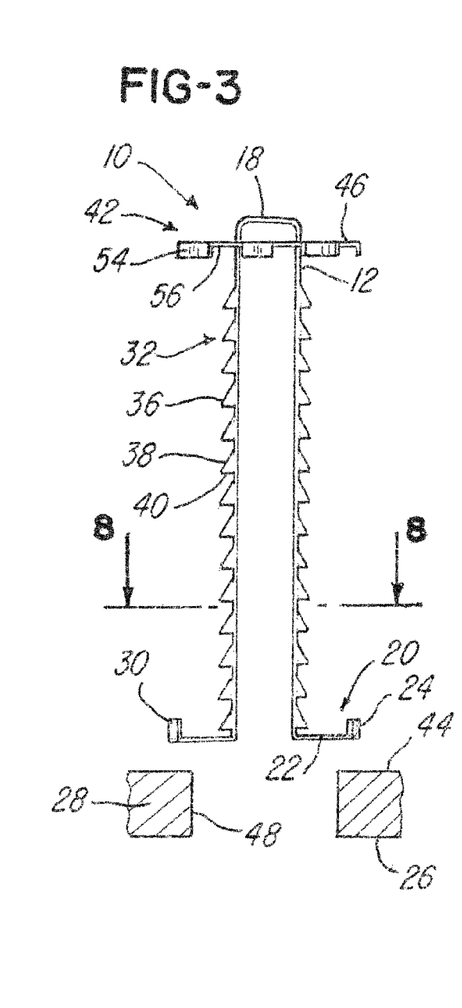
FIG. 3 is a side view of the cranial clamp depicted in FIG. 1, where the clamp is located above an aperture in a bone and the first ends of the flexible anchoring members are in an initial or spaced position.
Figure 4:
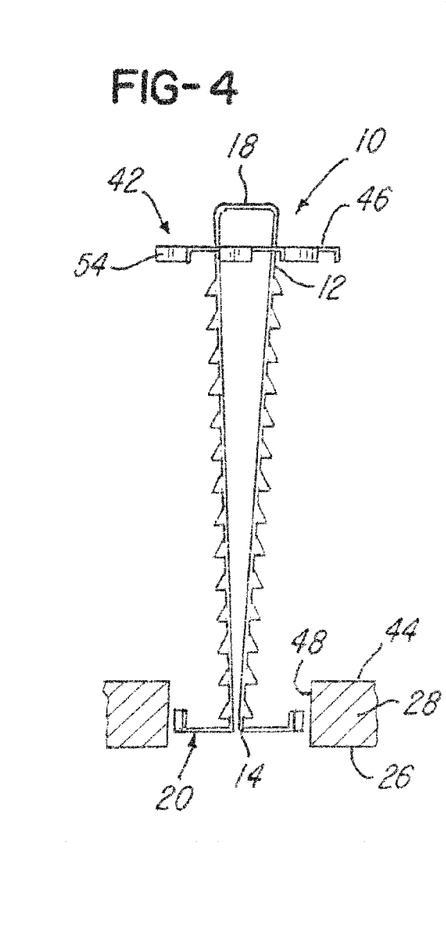
FIG. 4 is a side view of the cranial clamp similar to that depicted in FIG. 3, where the stabilizing member is in a position adjacent the second ends of the flexible anchoring members and the first ends of the flexible anchoring members are brought together or compressed so as to permit insertion through the aperture in the bone.

Referring now to the drawings in detail, wherein identical numerals indicate the same elements throughout the figures, FIG. 1 depicts a flexible clamp device 10 which may be utilized for covering or plugging a burr hole or the like in a bone (e.g., a skull or cranium). It will be seen that flexible clamp device 10 preferably includes a plurality of flexible, elastic or resilient anchoring members 12, each having a first or anchoring end 14 and a second end 16 opposite thereof. As seen in FIG. 1, each flexible anchoring member 12 comprises an elongated body, substantially rectangular in shape, and has a relatively thin thickness so as to enable flexing. A cross member 18 is provided to integrally connect second ends 16 of flexible anchoring members 12. In this way, such second ends 16 are maintained at a predetermined spacing. By contrast, first ends 14 are not connected and therefore adjustable, elastic or flexible and moveable between a spaced position similar to that at second ends 16 (FIG. 3) and a compressed position where such first ends 14 are displaceable inwardly so as to be in close proximity (FIG. 4) to each other.

Figure 5:
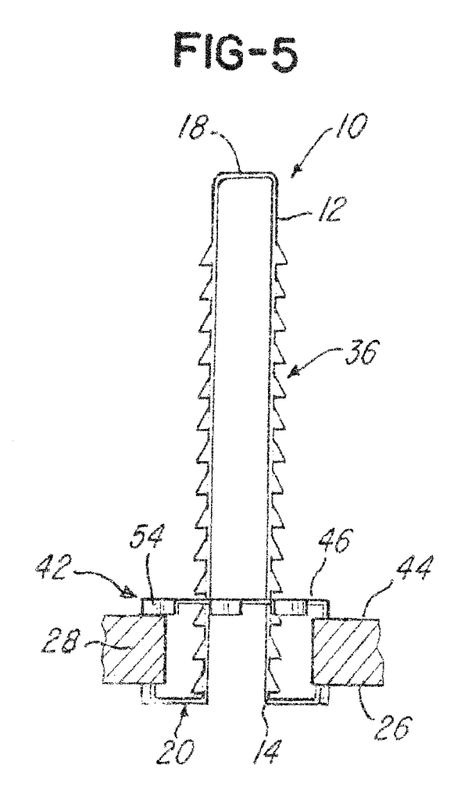
FIG. 5 is a side view of the cranial clamp similar to that depicted in FIGS. 3 and 4, where the stabilizing member has been positioned adjacent the first ends of the flexible anchoring members so as to be engagingly positioned against an outer surface of the bone, the flexible arms have been expanded to their original spaced position, and the locking tabs associated with the first ends of the flexible anchoring members are engagingly positioned against an inner surface of the bone.
Figure 6:
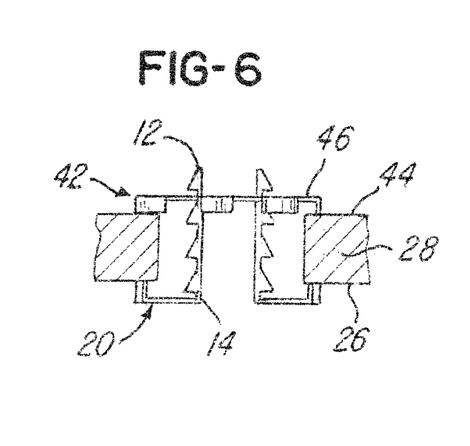
FIG. 6 is a side view of the cranial clamp similar to that depicted in FIG. 5, where the upper portions of the flexible anchoring members have been trimmed immediately above the stabilizing member.

It will further be seen that each anchoring end 14 comprises a locking tab 20. The locking tabs 20, as shown, include a first locking tab portion 22 extending outwardly from and substantially perpendicular to first end 14, and a second locking tab portion 24 that extends from first locking tab portion 22 toward second end 16 of flexible anchoring member 12 as shown. It will be appreciated that first locking tab portions 22 of flexible anchoring members 12 may be sized to accommodate use of flexible clamp device 10 with apertures of varying size in cranial bone 28. Second locking tab portion 24 functions to contact an inner surface 26 of cranial bone 28, as depicted in FIGS. 5 and 6, and may be oriented substantially perpendicular to first locking tab portion 22 or at any preferred angle of engagement. While not shown, an edge or surface 30 of second locking tab portion 24 may be tapered or extended to enhance engagement with cranial bone inner surface 26.

Figure 2:
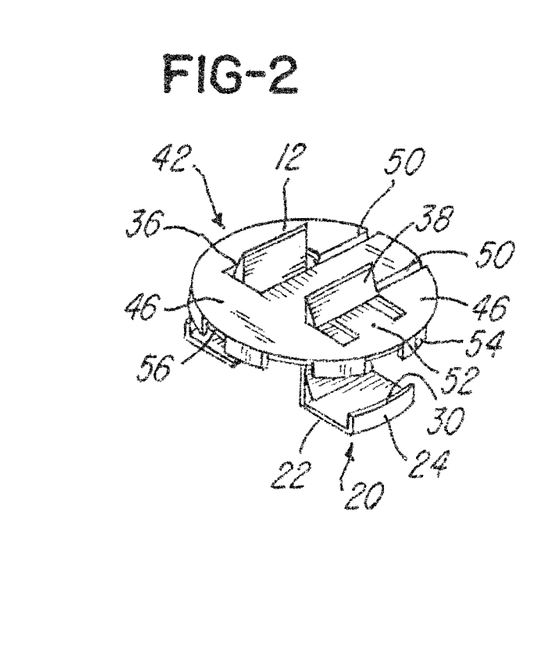
FIG. 2 is a perspective view of the cranial clamp depicted in FIG. 1, where the stabilizing member is in a position adjacent the first ends of the flexible anchoring members and the flexible anchoring members have been trimmed.
Figure 8:
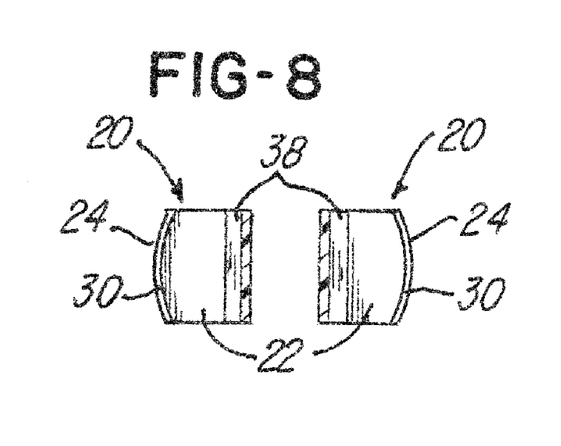
FIG. 8 is a sectional view taken along the line 8-8 in FIG. 3.

Each flexible anchoring member 12 also preferably includes a ratcheting mechanism 32 positioned along an outer surface 34 thereof. Such ratcheting mechanism 32 generally will include a plurality of ratchets or teeth 36 spaced along flexible anchoring member 12. For reasons discussed herein, it is preferred that such teeth 36 include a first surface 38 (FIGS. 2 and 8) which is oriented so as to be angled or ramped in a direction toward first end 14 of flexible anchoring member 12 and a second surface 40 which is oriented substantially perpendicular to flexible anchoring member 12. In this way, it will be seen that ratcheting mechanism 32 is designed to permit movement therealong in one direction (i.e., unilaterally from second ends 16 to first ends 14), while preventing or restricting movement in an opposite direction.

Figure 7:
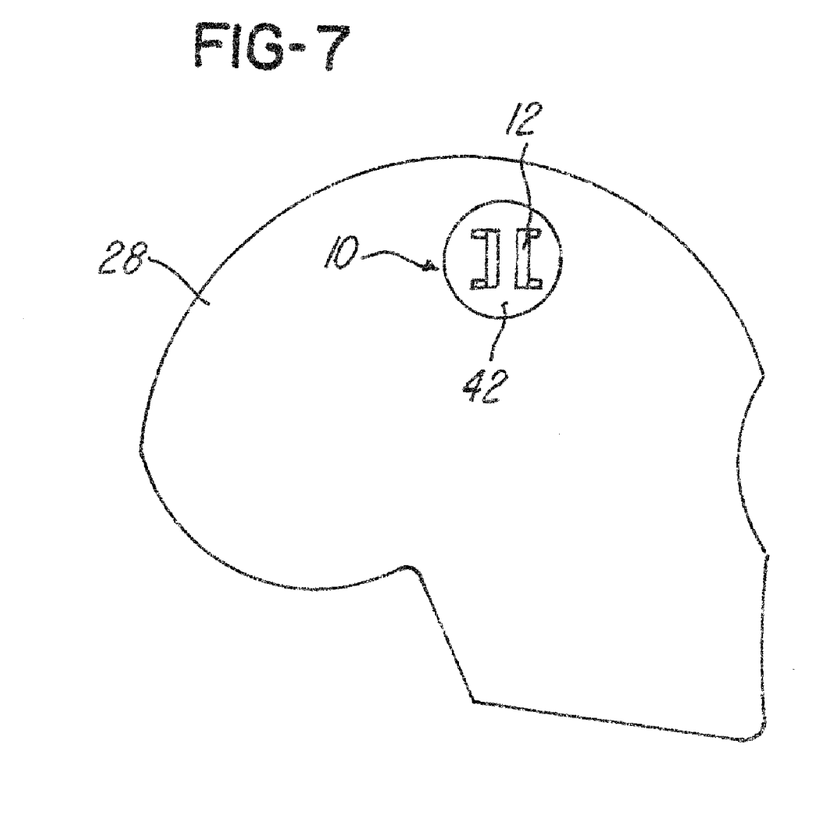
FIG. 7 is a diagrammatic view of the cranial clamp depicted in FIG. 6 positioned with respect to a burr hole in a skull.

Flexible clamp device 10 further includes a stabilization member 42 (FIG. 2) which slidingly receives the flexible anchoring members 12 as shown. Accordingly, stabilization member 42 is able to be translocated from a first position adjacent second ends 16 of flexible anchoring members 12 (see FIGS. 3 and 4) to a second position adjacent first ends 14 thereof (see FIGS. 5, 6 and 7). It will be appreciated that first ends 14 of flexible anchoring members 12 will be able to be compressed or displaced inwardly when stabilization member 42 is located adjacent second ends 16. As stabilization member 42 is translocated closer to first ends 14 of flexible anchoring members 12, however, the ability of first ends 14 to be compressed decreases. When stabilization member 42 is translocated to the point where it engages an outer surface 44 of cranial bone 28, a rigid clamp is formed with locking tabs 20 and first ends 14 of flexible anchoring members 12 is maintained in a spaced position (see FIG. 5).

More specifically, it will be seen that stabilization member 42 preferably includes a substantially planar member 46 that has a predetermined size and shape that may be useful for covering a particular aperture 48 (FIG. 3) in cranial bone 28. An inventory of planar members 46 may be interchangeable with flexible anchoring members 12 to accommodate several sizes and shapes of apertures.

Further, a plurality of slits 50 are preferably formed in planar member 46 so as to permit stabilization member 42 to receive and engage flexible anchoring members 12. While planar member 46 may be slid laterally into position between adjacent teeth 36 of ratcheting mechanisms 32 to form the clamp with locking tabs 20, it is preferred that a plurality of pawl members 52 be formed in planar member 46 which are accessible via slits 50. This enables such pawl members 52 to be aligned and engaged with teeth 36 of ratcheting mechanisms 32. In this way, stabilization member 42 is able to be translocated unidirectionally until it is positioned adjacent to first ends 14 of flexible anchoring members 12 and forms a clamp with locking tabs 20. Of course, it will be understood that pawl members 52 are able to slide or ratchet over first surface 38 of ratchet teeth 36 in a direction toward first ends 14 of flexible anchoring members 12, whereas second surface 40 of such ratchet teeth 36 functions as a stop to prevent translocation of stabilization member 42 in a direction toward second ends 16 of flexible anchoring members 12.

A plurality of locking teeth 54 preferably extend from a lower surface 56 of planar member 46 in order to better engage outer surface 44 of cranial bone 28. Locking teeth 54 are preferably positioned intermittently around planar member lower surface 56 and may be sized and/or angled as desired.

With regard to the construction of flexible clamp device 10, it is preferred that a pair of flexible anchoring members 12 be formed and connected at second ends 16 thereof by means of the cross member 18. Locking tabs 20 are preferably formed at first ends 14 of flexible anchoring members 12, where first and second locking tab portions 22 and 24, respectively, may be formed, molded, machined, stamped or otherwise created. In addition, ratchet teeth 36 may be created in flexible anchoring members 12 by puncturing the walls thereof or otherwise attached thereto. Accordingly, this enables all such components to be a one-piece construction, which could simplify manufacturing of flexible clamp device 10.

A method of positioning a flexible clamp device 10 within an aperture 48 of a cranial bone 28 is also provided by the present invention, where flexible clamp device 10 includes a plurality of flexible anchoring members 12 and a stabilization member 42 slidingly engagable therewith. This method includes the following steps: maintaining second ends 16 of flexible anchoring members 12 in a predetermined spaced position; flexing first ends 14 of flexible anchoring members 12 from a predetermined spaced position wider than aperture 48 to a compressed position more narrow than aperture 48; inserting first ends 14 of flexible anchoring members 12 through aperture 48 in cranial bone 28; expanding first ends 14 of flexible anchoring members 12 away from each other from the compressed position to the predetermined spaced position so as to engage an inner surface 26 of cranial bone 28; and, translocating stabilization member 42 from adjacent second ends 16 of flexible anchoring members 12 to a position adjacent first ends 14 thereof so as to engage an outer surface 44 of cranial bone 28. Once stabilization member 42 is in a clamping position adjacent first ends 14, the method preferably includes the step of locking stabilization member 42 in position. Additional steps of the method preferably include associating locking tabs 20 with first ends 14 of flexible anchoring members 12 and trimming flexible anchoring members 12 after stabilization member 42 engages outer surface 44 of cranial bone 28 at a point immediately above stabilization member 42.

Further, the method generally will include the step of engaging stabilization member 42 with flexible anchoring members 12, such as by means of slits 50 as described herein. It will be appreciated that stabilization member 42 may be positioned in sliding engagement with flexible anchoring members 12 either before or after first ends 14 thereof are inserted through aperture 48.

Additionally, the flexing step of the method may be performed either manually or by means of a clamping instrument specially designed for the purpose. Likewise, translocation of stabilization member 42 according to the method may be performed either manually or via a clamping instrument.

Having shown and described the preferred embodiment of the present invention, further adaptations of flexible clamp device 10, flexible anchoring members 12, stabilization member 42, and the other components thereof can be accomplished by appropriate modifications by one of ordinary skill in the art without departing from the scope of the invention. Moreover, it will be understood that further adaptations of the method steps for positioning the flexible clamp device 10 within an aperture 48 of a cranial bone 28 may be accomplished by appropriate modifications by one of ordinary skill in the art.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A flexible clamp device for the anchoring of cranial bones, comprising:
   a plurality of flexible anchoring members;
   a stabilization member having a generally planar member and at least one locking tooth or projection extending from said stabilization member and adapted to engage an exterior portion of a cranial bone, said stabilization member is adapted to be mounted on said plurality of flexible anchoring members in a direction that is generally radial or generally perpendicular to a longitudinal axis of said plurality of flexible anchoring members;
   wherein said plurality of flexible anchoring members are spaced and each comprise an anchoring end adapted to clamp to an internal portion of said cranial bone;
   a cross member monolithically formed with said plurality of flexible anchoring members and connecting second ends of each of said plurality of flexible anchoring members, wherein each of said plurality of flexible anchoring members may be flexed such that said anchoring ends thereof are displaced inwardly toward each other to facilitate placement through an aperture in said cranial bone and adapted to flex away from each other after said placement so that said anchoring ends become situated in opposed relation to said internal portion of said cranial bone;
   a locking tab extending from said anchoring end of each of said plurality of flexible anchoring members and being adapted to engage and clamp against an internal surface of a cranial bone, said locking tab further comprising:
      a first portion extending outwardly from said anchoring end; and
      a second portion extending generally perpendicular from said first portion toward said second end, said second portion engaging said internal portion of said cranial bone;
   said first and second portions also being monolithically formed together with said plurality of flexible anchoring members which are monolithically formed with said cross member.

2. The flexible clamp device as recited in claim 1, wherein each of said plurality of flexible anchoring members is an elongated body having an anchoring end and a second end opposite thereof.

3. The flexible clamp device as recited in claim 1, wherein said plurality of flexible anchoring members each comprise elongated bodies comprising unidirectional ratcheting mechanisms.

4. The flexible clamp device as recited in claim 1, wherein said plurality of flexible anchoring members are spaced apart a predetermined amount and each comprise an anchoring end having locking tabs adapted to clamp to an internal portion of a cranial bone.

5. The flexible clamp device as recited in claim 1, wherein said plurality of flexible anchoring members each having a generally elongated body.

6. The flexible clamp device as recited in claim 1, wherein said stabilization member incorporates a plurality of pawl mechanisms to receive said plurality of flexible anchoring members.

7. The flexible clamp device as recited in claim 1, wherein said stabilization member can be translocated such that each of said plurality of flexible anchoring members displaces locking members and locking tabs outward.

8. The flexible clamp device as recited in claim 1, wherein said stabilization member can be translocated such that said stabilization member constitutes a rigid clamp with locking members.

9. The flexible clamp device as recited in claim 1, wherein said stabilization member can be cut off following clamping of said stabilization member.

10. The flexible clamp device as recited in claim 2, further comprising a unidirectional ratcheting mechanism associated with each of said plurality of flexible anchoring members.

11. The flexible clamp device as recited in claim 10, said stabilization member further comprising a plurality of pawl mechanisms to receive said unidirectional ratcheting mechanism on each of said plurality of flexible anchoring members.

12. The flexible clamp device as recited in claim 11, said stabilization member further comprising a plurality of slits formed therein for receiving each of said plurality of flexible anchoring members.

13. The flexible clamp device as recited in claim 11, wherein said stabilization member can be translocated from a first position adjacent second ends of each of said plurality of flexible anchoring members to a second position adjacent said anchoring ends of each of said plurality of flexible anchoring members.

14. The flexible clamp device as recited in claim 13, wherein said stabilization member in the second position causes said anchoring ends of each of said plurality of flexible anchoring members to be maintained in a spaced position.

15. The flexible clamp device as recited in claim 13, wherein said stabilization member can be translocated to the second position so as to constitute a rigid clamp with said anchoring ends of each of said plurality of flexible anchoring members.

16. The flexible clamp device as recited in claim 15, said stabilization member further comprising a plurality of locking teeth extending from a lower surface thereof so as to engage an upper surface of a cranial bone.

17. The flexible clamp device as recited in claim 15, said anchoring end of each of said plurality of flexible anchoring members including a locking tab associated therewith so as to engage a lower surface of a cranial bone.

18. The flexible clamp device as recited in claim 1, said stabilization member further comprising:
   a substantially planar member slidingly engagable with each of said plurality of flexible anchoring members;

a plurality of locking teeth extending from a lower surface of said substantially planar member in spaced relation; and a mechanism for retaining said substantially planar member in a desired position along each of said plurality of flexible anchoring members.

19. The flexible clamp device as recited in claim 18, said retaining mechanism for retaining further comprising a plurality of pawl members formed in said substantially planar member for engaging corresponding ratcheting mechanisms provided on each of said plurality of flexible anchoring members.

20. A flexible clamp for plugging an aperture in a cranial bone, comprising:
a plurality of flexible elongated bodies, each of said plurality of flexible elongated bodies having a first end and a second end opposite said first end;
a locking tab integrally formed in said first end of each elongated body;
a stabilization member slidingly engagable with said plurality of flexible elongated bodies, wherein said stabilization member may be translocated from a first position to a clamping position adjacent said first ends of said plurality of flexible elongated bodies; and having a generally planar member and at least one locking tooth or projection extending from said stabilization member and adapted to engage an exterior portion of a cranial bone, said stabilization member is adapted to be mounted on said plurality of flexible anchoring members in a direction that is generally radial or generally perpendicular to a longitudinal axis of said plurality of flexible anchoring members;
a cross member monolithically formed with said plurality of flexible anchoring members and integrally connecting second ends of each of said plurality of flexible elongated bodies, wherein a plurality of flexible anchoring members are spaced apart a predetermined amount so that said plurality of flexible elongated bodies may be flexed toward each other to facilitate placement through the aperture in the cranial bone and adapted to flex away from each other after said placement so that said locking tabs become situated in opposed relation to an internal portion of said cranial bone;
wherein each of said locking tabs engages an inner surface of said cranial bone and said stabilization member engages an outer surface of said cranial bone when in the clamping position;
each of said locking tabs extending from said anchoring end of each of said plurality of flexible anchoring members and being adapted to engage and clamp against an internal surface of a cranial bone, said locking tabs further comprising:
a first portion extending outwardly from said anchoring end; and
a second portion extending generally perpendicular from said first portion toward said second end, said second portion engaging said internal portion of said cranial bone;
said first and second portions also being monolithically formed together with said plurality of flexible anchoring members which are monolithically formed with said cross member.

21. The flexible clamp recited in claim 20, wherein said cross member connects said second ends of said plurality of flexible elongated bodies in spaced relation.

22. The flexible clamp recited in claim 20, further comprising:
a ratcheting mechanism associated with each said elongated body; and
a plurality of pawl mechanisms formed within said stabilization member which lockingly engage with each of said ratcheting mechanisms.

23. The flexible clamp recited in claim 20, said stabilization member further comprising:
a substantially planar member slidingly engagable with said plurality of flexible elongated bodies; and
plurality of locking teeth extending from a lower surface of said substantially planar member in spaced relation which engage said outer surface of said cranial bone when said stabilization member is in the clamping position.

24. The flexible clamp recited in claim 20, wherein said first ends of said plurality of flexible elongated bodies are compressible when said stabilization member is positioned adjacent said second ends of said plurality of flexible elongated bodies.

25. The flexible clamp recited in claim 20, wherein said first ends of said plurality of flexible elongated bodies are maintained in spaced relation when said stabilization member is positioned adjacent thereto.

26. The flexible clamp recited in claim 22, wherein each of said ratcheting mechanisms associated with said plurality of flexible elongated bodies are unidirectional.

27. The flexible clamp recited in claim 20, said locking tab further comprising:
a first portion extending outwardly from said first end of said elongated body; and
a second portion extending from said first locking tab portion toward said second end of said elongated body.

28. The flexible clamp recited in claim 20, wherein said second ends of said plurality of flexible elongated bodies are spaced a predetermined amount.

29. The flexible clamp recited in claim 20, wherein said first ends of said plurality of flexible elongated bodies are adjustably spaced.

30. The flexible clamp recited in claim 29, wherein the position of said stabilization member along said plurality of flexible elongated bodies controls the amount of movement available at said first ends of said plurality of flexible elongated bodies.

31. The flexible clamp recited in claim 23, said substantially planar member of said stabilization member further including a plurality of slits formed partially therein for receiving said plurality of flexible elongated bodies.

32. The flexible clamp recited in claim 20, wherein said stabilization member is sized to be greater than a width of the aperture in said cranial bone.

33. The flexible clamp recited in claim 20, wherein said locking tabs of said plurality of flexible elongated bodies are movable between a position wider than said aperture to a position more narrow than said aperture.

34. A flexible clamp device for use with a cranial bone, comprising:
a first flexible anchoring member;
a second flexible anchoring member;
said first and second flexible anchoring members being adapted for positioning on said cranial bone; and
a stabilization member for slidably mounting on said first and second flexible anchoring members to cover a hole or opening in said cranial bone; having a generally planar member and at least one locking tooth or projection extending from said stabilization member and adapted to engage an exterior portion of a cranial bone, said stabilization member is adapted to be mounted on said plurality of flexible anchoring members in a direction that is generally radial or generally perpendicular to a longitudinal axis of said plurality of flexible anchoring members;

wherein said first and second flexible anchoring members being spaced apart a predetermined amount and each comprise an anchoring end having a locking clamp adapted to clamp to an internal portion of said cranial bone;

a cross member monolithically formed with said plurality of flexible anchoring members and integrally connecting second ends of said first and second flexible anchoring members, wherein each of said first and second flexible anchoring members may be flexed such that said anchoring ends move toward each other to facilitate placement through an aperture in said cranial bone and adapted to flex away from each other after said placement so that said locking clamps become situated in opposed relation to an internal surface of said cranial bone;

a locking tab extending from said anchoring end of each of said plurality of flexible anchoring members and being adapted to engage and clamp against an internal surface of a cranial bone, said locking tab further comprising:
 a first portion extending outwardly from said anchoring end; and
 a second portion extending generally perpendicular from said first portion toward said second end, said second portion engaging said internal portion of said cranial bone;

said first and second portions also being monolithically formed together with said plurality of flexible anchoring members which are monolithically formed with said cross member.

35. The flexible clamp device as recited in claim 34, wherein said first and second flexible anchoring members each comprise an elongated body having an anchoring end and a second end opposite thereof.

36. The flexible clamp device as recited in claim 35, wherein said first and second flexible anchoring members comprise a unidirectional ratcheting mechanism.

37. The flexible clamp device as recited in claim 34, wherein said first and second flexible anchoring members comprise a locking tab extending from said anchoring end of said first and second flexible anchoring members and being adapted to clamp to said internal surface of said cranial bone.

38. The flexible clamp device as recited in claim 37, wherein said locking clamp further comprises:
 a first portion extending outwardly from said anchoring end of each of said first and second flexible anchoring members; and
 a second portion extending from said first portion toward said second end of each of said first and second flexible anchoring members.

39. The flexible clamp device as recited in claim 36, wherein said stabilization member further comprises a plurality of pawl mechanisms to receive said unidirectional ratcheting mechanism on each of said first and second flexible anchoring members.

40. The flexible clamp device as recited in claim 39, wherein said stabilization member further comprises a plurality of slits formed therein for receiving each of said first and second flexible anchoring members.

41. The flexible clamp device as recited in claim 39, wherein said locking clamp is generally L-shaped in cross-section.

* * * * *